(12) United States Patent
Helmer

(10) Patent No.: US 10,842,947 B2
(45) Date of Patent: Nov. 24, 2020

(54) MEDICAMENT INJECTION DEVICE

(71) Applicant: SANOFI-AVENTIS DEUTSCHLAND GMBH, Frankfurt am Main (DE)

(72) Inventor: Michael Helmer, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 166 days.

(21) Appl. No.: 15/779,046

(22) PCT Filed: Nov. 21, 2016

(86) PCT No.: PCT/EP2016/078260
§ 371 (c)(1),
(2) Date: May 24, 2018

(87) PCT Pub. No.: WO2017/089271
PCT Pub. Date: Jun. 1, 2017

(65) Prior Publication Data
US 2018/0353704 A1    Dec. 13, 2018

(30) Foreign Application Priority Data

Nov. 27, 2015 (EP) .................................. 15196691

(51) Int. Cl.
*A61M 5/32* (2006.01)
*A61M 5/20* (2006.01)
*A61M 5/24* (2006.01)

(52) U.S. Cl.
CPC ........ *A61M 5/3204* (2013.01); *A61M 5/2033* (2013.01); *A61M 5/2466* (2013.01);
(Continued)

(58) Field of Classification Search
CPC .............. A61M 5/2466; A61M 5/3202; A61M 2005/2474
See application file for complete search history.

(56) References Cited

U.S. PATENT DOCUMENTS 3,401,693 A    9/1968  Cohen
10,335,535 B2 *  7/2019  Bengtsson .............. A61M 5/24
(Continued)

FOREIGN PATENT DOCUMENTS

| CN | 103269730 | 8/2013 |
|---|---|---|
| WO | WO 2015/062845 | 5/2015 |
| WO | WO 2015/117854 | 8/2015 |

OTHER PUBLICATIONS

PCT International Preliminary Report on Patentability in International Appln. No. PCT/EP2016/078260, dated May 29, 2018, 9 pages.

(Continued)

*Primary Examiner* — Laura A Bouchelle
(74) *Attorney, Agent, or Firm* — Fish & Richardson P.C.

(57) ABSTRACT

A medicament injection device includes a main body having a cartridge receiving part configured to hold a medicament cartridge; a needle holder holding a needle; a needle sleeve at least partially surrounding the needle holder and needle and axially movable relative to the main body; a removable transverse blocking member separating the cartridge receiving part and the needle holder; and a compressed spring arranged between the needle holder and a distal end of the needle sleeve so that, upon removal of the blocking member, the spring is released, thereby causing the needle carrier to move axially towards cartridge receiving part.

20 Claims, 5 Drawing Sheets

(52) U.S. Cl.
CPC ......... *A61M 5/3202* (2013.01); *A61M 5/3293* (2013.01); *A61M 2005/206* (2013.01); *A61M 2005/2013* (2013.01); *A61M 2005/2073* (2013.01); *A61M 2005/2474* (2013.01)

(56) References Cited

U.S. PATENT DOCUMENTS

| | | |
|---|---|---|
| 2009/0171311 A1 | 7/2009 | Genosar et al. |
| 2013/0090605 A1 | 4/2013 | O'Connor et al. |
| 2015/0196718 A1 | 7/2015 | Radmer et al. |

OTHER PUBLICATIONS

PCT International Search Report and Written Opinion in International Appln. No. PCT/EP2016/078260, dated Feb. 21, 2017, 14 pages.

\* cited by examiner

MEDICAMENT INJECTION DEVICE

CROSS REFERENCE TO RELATED APPLICATIONS

The present application is the national stage entry of International Patent Application No. PCT/EP2016/078260, filed on Nov. 21, 2016 and claims priority to Application No. EP 15196691.8, filed in on Nov. 27, 2015, the disclosures of which are expressly incorporated herein in entirety by reference thereto.

FIELD

The present disclosure relates to a medicament injection device.

BACKGROUND

Medicament injection devices can take various forms. One form uses a syringe, where medicament is stored in a hollow cylinder, typically formed of glass. The medicament is sealed from the environment with a plunger moveable within the cylinder, and a needle fluidly connected to the syringe's distal end. The needle must remain capped in order to maintain the medicament under sterile conditions.

Another form of injection device uses a cartridge instead of a syringe, the cartridge having a distal seal instead of the syringe's needle. Typically a patient connects a double-ended needle to the cartridge before injection, thereby piercing the cartridge's seal with the proximal tip of the double-ended needle.

While a cartridge can provide handling and storage advantages relative to syringes, they are not without shortcomings. For example, the attachment of a needle to the cartridge requires an additional step. This step can be problematic for patients with limited dexterity, poor coordination, or who have lost a degree of sensation in their hands. Even with such disadvantages, in certain situations it is desirable to provide an injection device in which the needle is kept separate from the medicament until such time as the patient wishes to commence the injection. The injection device described herein aims to overcome one or more problems associated with prior devices.

SUMMARY

In one embodiments a medicament injection device is provided, comprising a main body having a cartridge receiving part configured to hold a medicament cartridge; a needle holder holding a needle; a needle sleeve at least partially surrounding the needle holder and needle and axially movable relative to the main body; a removable transverse blocking member separating the cartridge receiving part and the needle holder; and a compressed spring arranged between the needle holder and a distal end of the needle sleeve so that, upon removal of the blocking member, the spring is released, thereby causing the needle carrier to move axially in a proximal direction towards the cartridge receiving part.

The may further comprise a cap covering a distal portion of the device.

The cap may have a locking member arranged to interlock with a recess in the removable blocking member to prevent removal of the removable blocking member until the cap is at least partially removed.

The cap may comprise an inwardly extending part having a bore to substantially seal a distal end of the needle.

The spring may be further configured to cause the needle and needle hub to retract subsequent to injection of a medicament.

The cartridge receiving part and the needle holder may be arranged to form a frictional fit subsequent to axial movement of the needle holder towards the cartridge receiving part.

The cartridge receiving part may comprise a protruding part and the needle hub comprises a recessed part arranged to receive the protruding part of the cartridge receiving part.

The spring may be a helical spring.

The may further comprise a medicament cartridge containing a medicament and having a penetrable barrier across a distal end thereof and wherein axial movement of the needle carrier causes the needle to pierce the penetrable barrier.

The medicament cartridge may contain a medicament.

The device may be an auto-injector device.

In another embodiment a method of operating a medicament injection device is provided, the method comprising: removing a removable transverse blocking member from the device, thereby releasing a spring and causing the needle holder to move proximally into contact with the medicament cartridge and causing the needle to pierce the penetrable barrier.

The method may further comprise at least partially removing a cap from the device in order to release the transverse blocking member prior to removing the transverse blocking member.

BRIEF DESCRIPTION OF THE DRAWINGS

Exemplary embodiments of the present invention are described with reference to the accompanying drawings, in which.

DETAILED DESCRIPTION

Figure 1A:
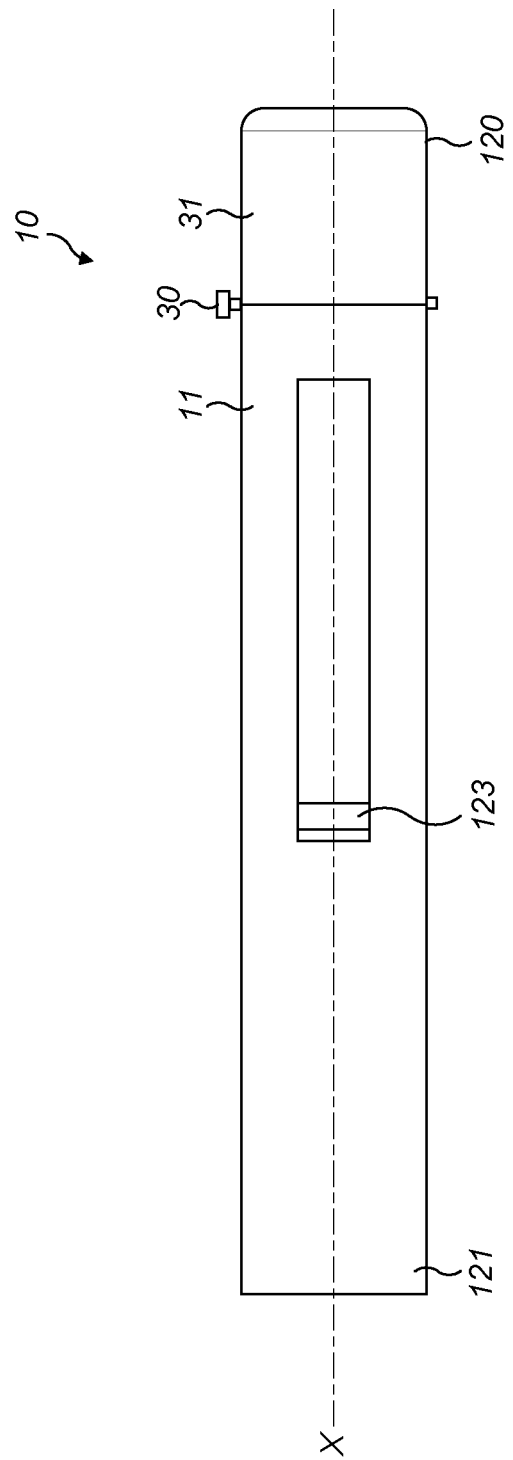
FIG. 1A is a side-on view of an injection device.

Exemplary embodiments of the current disclosure provide a mechanism for inserting a needle of an injection device into a cartridge containing a medicament for injection by a patient or care giver. The mechanism allows the medicament cartridge to remain sealed until such time as the user wishes to commence the injection. Automating a mechanism for inserting the needle into the medicament cartridge also reduces the amount of handling of the needle by the user prior to the injection. Indeed, in some embodiments described below, the user does not touch the needle when the needle is inserted into the medicament cartridge. For example, one mechanism for inserting the needle into the medicament cartridge described below involves removing a blocking element, thereby releasing a compressed spring to push the needle towards the medicament cartridge.

This disclosure describes mechanisms and methods for use with injection devices (e.g., auto-injectors, pen-injectors, manual injectors) where a double-ended needle can be connected to a cartridge when the user activates a piercing unit before injection.

In some embodiments, an additional step by the user is necessary. To prevent an unintentional setting by the user, the cartridge piercing cannot be started before the cap is removed or at least partially displaced.

The system provides improved needle safety and protection of the medicament against environmental conditions.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device. The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle sleeve in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
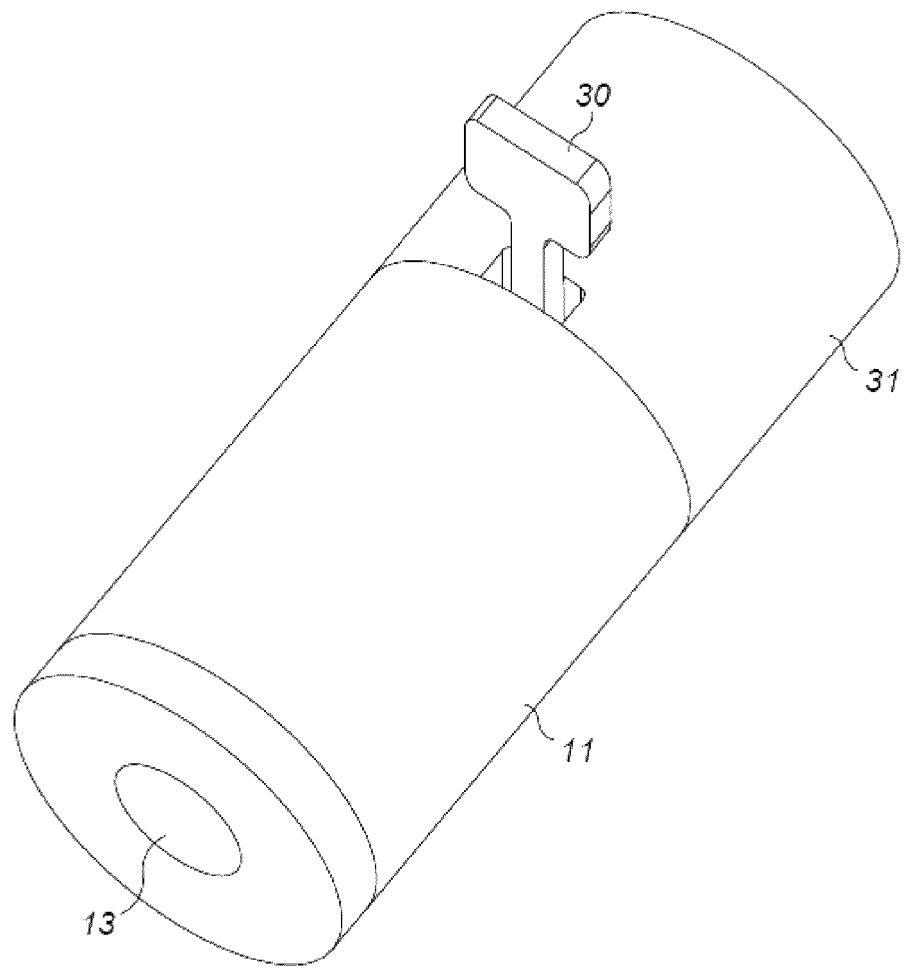
FIG. 1B is a perspective view of the injection device.

According to some embodiments of the present disclosure, an exemplary drug delivery device 10 is shown in FIGS. 1A & 1B. Device 10, as described above, is configured to inject a medicament into a patient's body. Device 10 includes a main body 11 which typically contains a reservoir containing the medicament to be injected (e.g., a syringe) and the components required to facilitate one or more steps of the delivery process. Device 10 can also include a cap assembly 31 that can be detachably mounted to the main body 11. Typically a user must remove cap 31 from main body 11 before device 10 can be operated.

As shown, main body 11 is substantially cylindrical and has a substantially constant diameter along the longitudinal axis X. The main body 11 has a distal region 120 and a proximal region 121. The term "distal" refers to a location that is relatively closer to a site of injection, and the term "proximal" refers to a location that is relatively further away from the injection site.

Device 10 can also include a needle sleeve 24 coupled to main body 11 to permit movement of sleeve 24 relative to main body 11. For example, sleeve 24 can move in a longitudinal direction parallel to longitudinal axis X. Specifically, movement of sleeve 24 in a proximal direction can permit a needle 17 to extend from distal region 120 of main body 11.

Insertion of needle 17 can occur via several mechanisms. For example, needle 17 may be fixedly located relative to main body 11 and initially be located within an extended needle sleeve 24. Proximal movement of sleeve 24 by placing a distal end of sleeve 24 against a patient's body and moving main body 11 in a distal direction will uncover the distal end of needle 17. Such relative movement allows the distal end of needle 17 to extend into the patient's body. Such insertion is termed "manual" insertion as needle 17 is manually inserted via the patient's manual movement of main body 11 relative to sleeve 24.

Another form of insertion is "automated," whereby needle 17 moves relative to main body 11. Such insertion can be triggered by movement of sleeve 24 or by another form of activation, such as, for example, a button. As shown in FIGS. 1A & 1B, button is located at a proximal end of main body 11. However, in other embodiments, button could be located on a side of main body 11.

Other manual or automated features can include drug injection or needle retraction, or both. Injection is the process by which a bung or piston 123 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 121 of main body 11, and a distal end of the drive spring can be configured to apply a compressive force to a proximal surface of piston 123. Following activation, at least part of the energy stored in the drive spring can be applied to the proximal surface of piston 123. This compressive force can act on piston 123 to move it in a distal direction. Such distal movement acts to compress the liquid medicament within the syringe, forcing it out of needle 17.

Following injection, needle 17 can be retracted within the sleeve 24. Retraction can occur when sleeve 24 moves distally as a user removes device 10 from a patient's body. This can occur as needle 17 remains fixedly located relative to main body 11. Once a distal end of sleeve 24 has moved past a distal end of needle 17, and needle 17 is covered, sleeve 24 can be locked. Such locking can include locking any proximal movement of sleeve 24 relative to main body 11.

Figure 2:
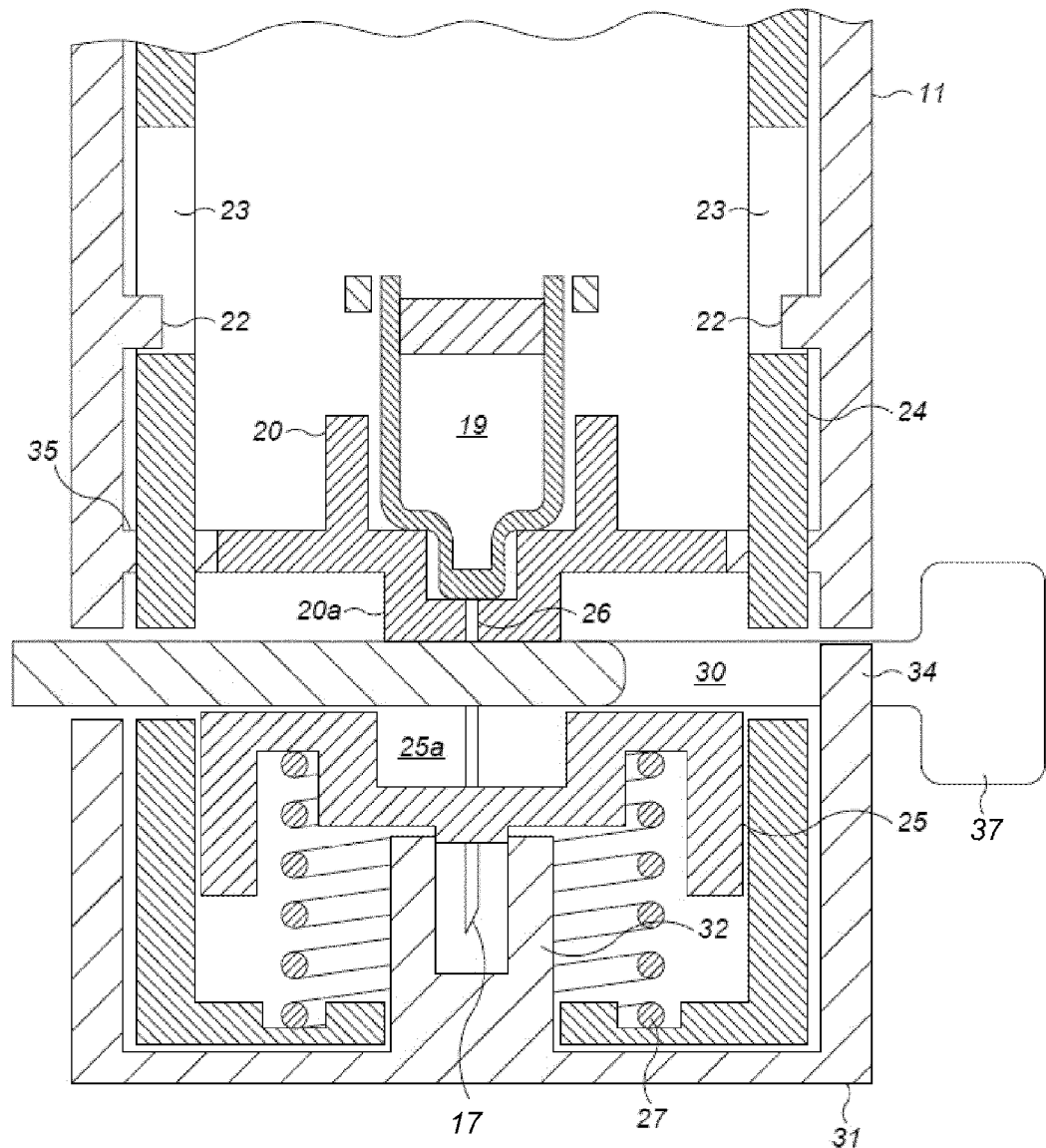
FIG. 2 is a cross sectional view of a distal end of the injection device shown in FIG. 1.

FIG. 2 shows a cross sectional view of the distal end of an injection device 10. The device 10 can include a generally tubular body 11 which functions to contain or provide coupling to a medicament cartridge 19, a needle sleeve 24 and a power unit (not shown). In some embodiments, the medicament cartridge 19 is fixed relative to the body 11 and can be held in place by a cartridge receiving part 20 which holds the medicament cartridge when inserted. The cartridge receiving part 20 may be formed as an integral part of the body 11 or it may be a separate module fitted to the body 11. The cartridge 19 may be generally cylindrical in shape. However, alternative shapes may be employed.

The needle sleeve 24 is a protective sleeve that prevents unwanted exposure of the needle 17 to a user. The needle sleeve 24 has a generally similar shape to the body 11 and is generally tubular. The needle sleeve 24 fits inside the body 11.

The generally tubular needle sleeve 24, coaxial with respect to the body 11, extends along an inner surface of the body 11. The main body 11 is arranged to be slidable in an axial direction with respect to the needle sleeve 24.

The cartridge receiving part 20 20 can be provided with a protruding part 20a having a passage 26 extending therethrough for receiving the needle 17 during insertion of the needle 17 into the medicament cartridge 19. The cartridge receiving part 20 comprises a surface extending transversely from the circumferential wall of the main body 11. The transverse surface of the cartridge receiving part 20 is provided with slots 35 to allow the needle sleeve 24 to pass therethrough, and move with respect to the main body 11 in use. The needle sleeve 24 is also provided with longitudinal slots (not shown) to allow the transverse surface of the cartridge receiving part 20 to connect to the circumferential wall of the main body 11. This configuration allows the main body 11 and needle sleeve 24 to fit together.

The medicament cartridge 19 is sealed at the distal end thereof by a penetrable septum.

The body 11 is provided with protrusions 22 extending inwardly from the interior surface of the body 11. The protrusions 22 are arranged to cooperate with corresponding recesses 23 located in the needle sleeve 24. The cooperation between the protrusions 22 and the edge of the recesses helps to prevent premature firing of the device 10 by preventing unwanted axial movement.

A needle hub 25 holds the needle 17. The needle hub has a cup shaped portion 25a which is configured to fit tightly around the protruding part 20a of the cartridge receiving part 20. The close fit allows for attachment between the needle hub 25 and the medicament cartridge 19. The needle hub 25 also has a protruding part 25b arranged around the periphery of the proximal end of the needle hub 25. The protruding part 25b is arranged to engage with the cartridge receiving part 20 between the protruding part 20a and the wall of the needle sleeve 24.

Both ends of the needle 17 are sharp (i.e., needle 17 is a double-ended or double-tipped needle). The distal end of the needle is sufficiently sharp to penetrate the patient's skin during the injection. The proximal end is sufficiently sharp to allow penetration of the cartridge septum.

A compressed spring 27 extends between the needle hub 25 and an inner face of the distal end of the needle sleeve 24. The spring 27 may be a helical spring or any other suitable spring, such as a wave spring, that allows the distal end of the needle 17 to extend through a central portion thereof.

A blocking element 30 is provided between the needle hub 25 and the medicament cartridge 19 to prevent piercing of the septum of the medicament cartridge 19 before the user is ready to conduct the injection. The blocking element 30 pushes against the needle hub 25 and acts to compress the spring 27. The blocking element 30 is removable and can slide out of an aperture 36 in the needle sleeve 24. The blocking element 30 may be provided with a gripping portion 37 to allow a user to grip the blocking element 30.

The device 10 is provided with a cap 31. The cap 31 covers the distal portion of the device 10. The cap 31 comprises an inwardly extending part 32 extending through an aperture 33 in the distal end of the needle sleeve 24. The inwardly extending part 32 has a bore therein to receive the distal end needle of the needle 17. The inwardly extending part 32 thus provides effective protection of the distal end of the needle 17 to reduce contamination thereof.

The cap 31 is provided with a pin 34 extending into a recess 35 of the blocking element 30. The engagement of the pin 34 with the recess 35 prevents the blocking member 30 from being removed until the cap 31 is pulled away by at least the distance corresponding to the length of the pin 34.

Figure 3:
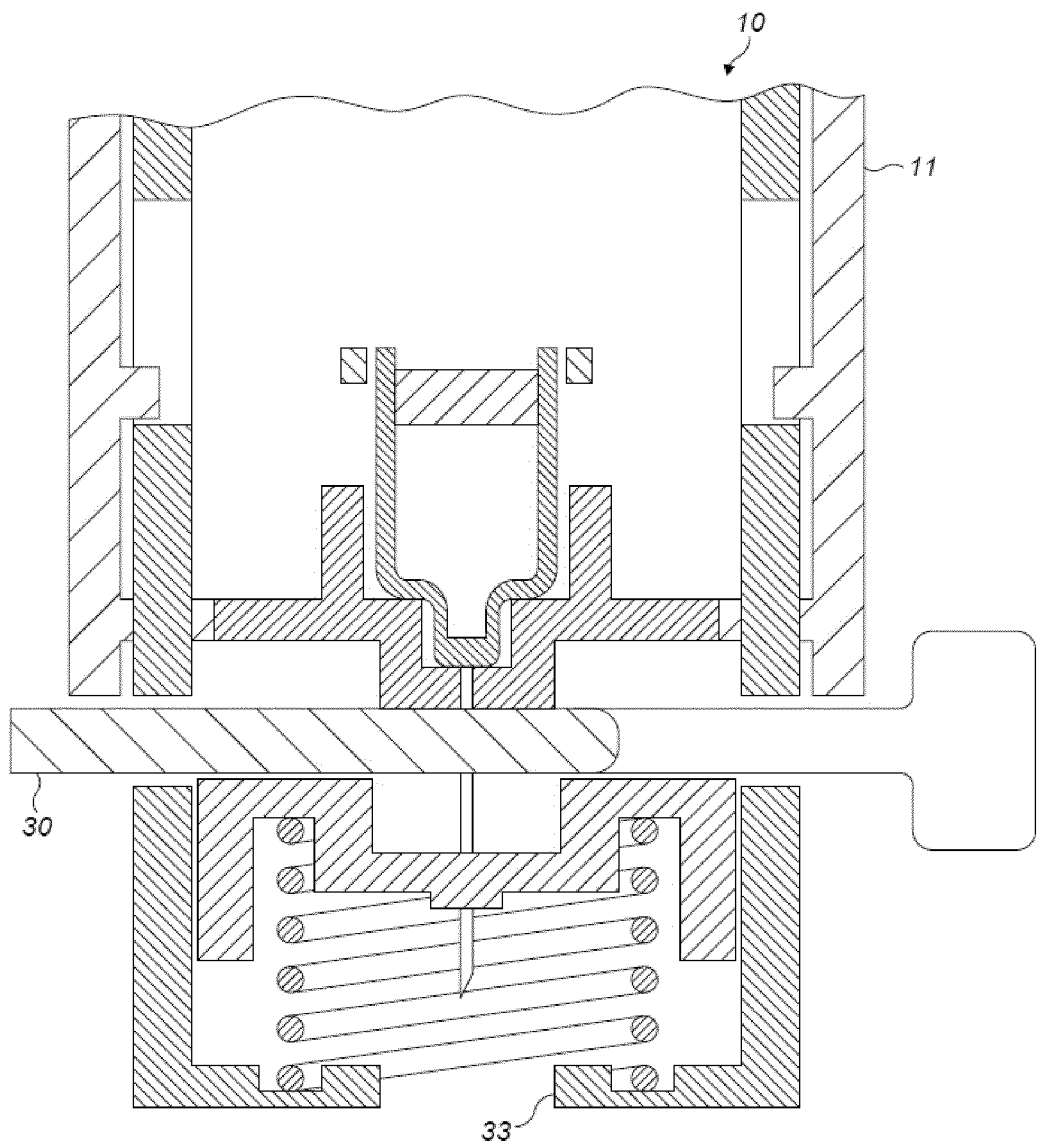
FIG. 3 is a cross sectional view of a distal end of the injection device after the cap has been removed.

FIG. 3 shows the device 10 shown in FIG. 2, whereby the cap 31 has been removed. To insert the needle 17 into the medicament 19 the user then removes the blocking element 30.

Figure 4:
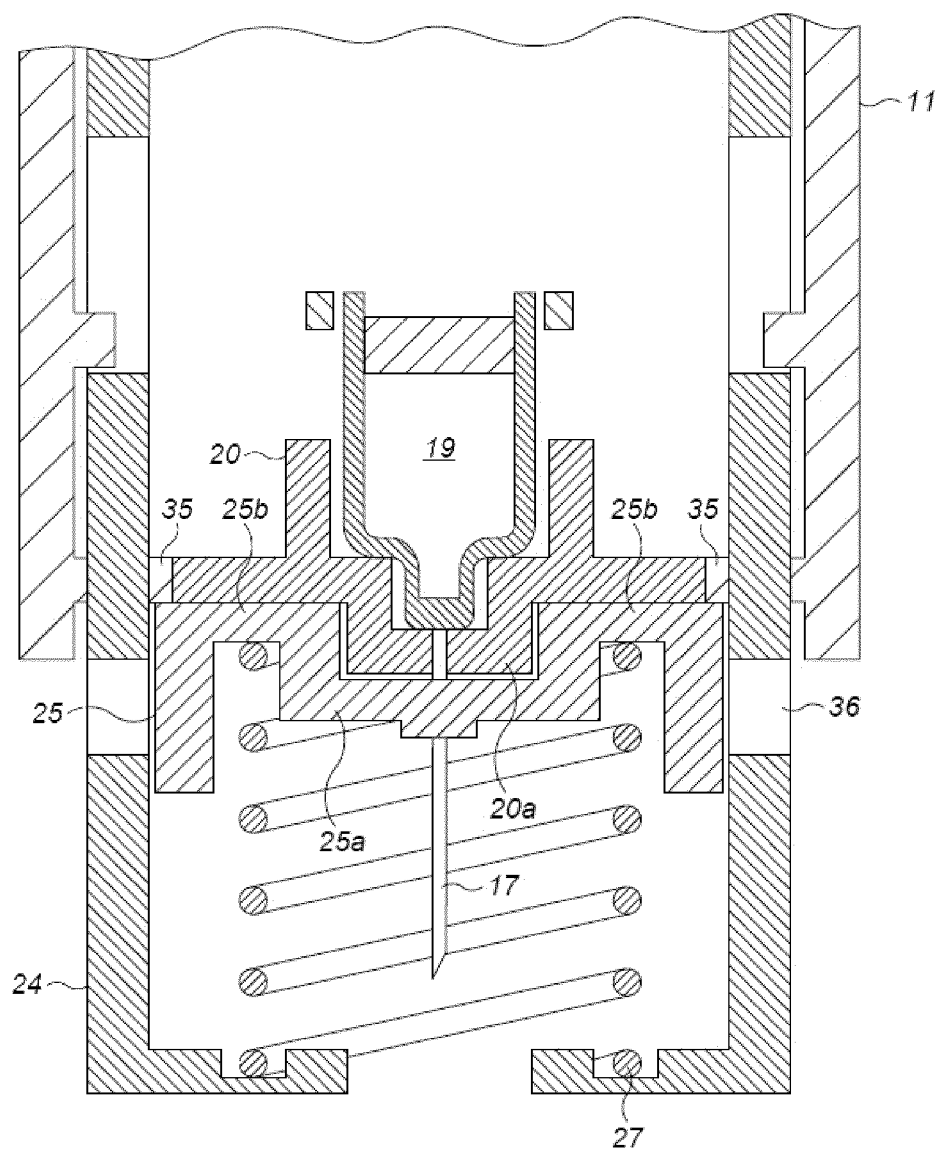
FIG. 4 is a cross sectional view of a distal end of the injection device after the blocking element has been removed.

FIG. 4 shows the device 10 after the blocking element 30 has been removed by the user. This step is typically performed immediately prior to the injection.

Once the blocking element 30 is removed, the spring 27 is released and causes the needle hub to be driven axially towards the medicament cartridge. The needle 17 pierces the septum. The cup shaped part 25a of the needle hub 25 fits over the protruding part 20a of the medicament cartridge receiving part 20 to form a frictional fit.

The injection of medicament into the patient can then commence. The user places the distal end of the device 10 against the patient's injection site. The user then actuates the device 10 by pushing the dispense button 13. Actuation of the device 10 causes the main body 11 to disengage from the needle sleeve 24. The protrusions 22 disengage from the respective recesses 23, allowing for relative axial movement of the main body 11 with respect to the needle sleeve 24. The disengagement of the main body 11 from the needle sleeve 24 is caused by the drive mechanism of the device 10.

In alternative embodiments, instead of actuating the device using the dispense button 13, the device may be actuated by axial movement of the needle sleeve 24 with respect to the main body 11.

The main body 11, medicament cartridge receiving part 20, medicament cartridge 19, needle hub 25 and needle 17 are pushed axially towards the injection site by a drive mechanism of the device 10. The axial movement of the needle hub 25 towards the distal end of the device 10 causes a compression of the spring 27.

The needle 17 emerges from the aperture 33 in the needle sleeve 24 and pierces the patient's skin. The piston 14 is actuated and expels the medicament from the medicament cartridge 19, through the passage in the cartridge receiving part 20 and through the needle 17, thereby causing the medicament to be injected into the patient. Once the device 10 determines that the injection is complete, the axial force pushing the main body 11, needle 17, needle hub 25 and medicament cartridge 19 towards the distal end is released.

The release of the axial force towards the distal end of the device 10 releases the compressive force on the spring 27. The spring 27 thus reverts to its equilibrium position, thereby causing the needle 17 and needle hub 25 to retract inside the needle sleeve 24.

The spring 27 therefore performs a dual role. Firstly, the spring is compressed by the blocking element 30 and is separated from the medicament cartridge 19. Once the blocking element 30 is released, the spring 27 causes the needle hub 25 and needle 17 to connect with the medicament cartridge 19. Secondly, the needle spring is compressed by movement of the main body 11, medicament holder 20 and needle hub 25. After the injection has been completed the downward force towards the distal end of the device 10 is released, causing the spring to revert to it equilibrium and the needle 17 to retract.

The skilled person will recognise several advantages of the device described above. The devices allow the needle to be stored separately from the medicament until such time as the user wishes to commence the injection. During the storage phase, the needle is contained within the cap so that the chances of it being contaminated before use are reduced in comparison with prior art devices. Accidental actuation of the piercing mechanism is prevented by the pin located in the cap so that the cap has to be at least partially removed before the blocking element is removed. The device is easy to operate. Users can cause the needle to pierce the septum and become attached to the medicament cartridge without the need for handling the needle. This also further reduces the risk of contaminating the needle prior to injection.

While embodiments of the invention have been described with respect to auto-injectors, it should be borne in mind that the invention is also applicable to alternative injection devices, for example syringes, pen-injectors, manual injectors, spinal injection systems etc. The mechanism for attaching the needle to the medicament cartridge may be employed in any injection device where it is desirable to keep the needle separate from the medicament until shortly before the injection.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15$^{th}$ edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten. An example of an oligonucleotide is, for example: mipomersen sodium (Kynamro®), a cholesterol-reducing antisense therapeutic for the treatment of familial hypercholesterolemia. Examples of DPP4 inhibitors are Vildagliptin, Sitagliptin, Denagliptin, Saxagliptin, Berberine. Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. A medicament injection device comprising:
   a main body having a cartridge receiving part configured to hold a medicament cartridge;
   a needle holder holding a needle;
   a needle sleeve at least partially surrounding the needle holder and needle and axially movable relative to the main body;
   a removable transverse blocking member separating the cartridge receiving part and the needle holder; and
   a compressed spring arranged between the needle holder and a distal end of the needle sleeve so that, upon removal of the transverse blocking member, the spring is released, thereby expanding to cause the needle holder to move axially in a proximal direction towards the cartridge receiving part.

2. The medicament injection device of claim 1, further comprising a cap covering a distal portion of the medicament injection device.

3. The medicament injection device of claim 2, wherein the cap has a locking member arranged to interlock with a recess in the transverse blocking member to prevent removal of the transverse blocking member until the cap is at least partially removed.

4. The medicament injection device of claim 3, wherein the locking member comprises a pin extending into the recess of the transverse blocking member to prevent removal of the transverse blocking member until the cap is at least partially removed.

5. The medicament injection device of claim 4, wherein the pin is movable away from the transverse blocking member to enable the transverse blocking member to be removed.

6. The medicament injection device of claim 3, wherein the main body comprises protrusions extending inwardly from an interior surface of the main body.

7. The medicament injection device of claim 2, wherein the cap comprises an inwardly extending part having a bore to substantially seal a distal end of the needle.

8. The medicament injection device of claim 1, wherein the spring is further configured to cause the needle and needle holder to retract subsequent to injection of a medicament.

9. The medicament injection device of claim 1, wherein the cartridge receiving part and the needle holder are arranged to form a frictional fit subsequent to axial movement of the needle holder towards the cartridge receiving part.

10. The medicament injection device of claim 9, wherein the cartridge receiving part comprises a protruding part and the needle holder comprises a recessed part arranged to receive the protruding part of the cartridge receiving part.

11. The medicament injection device of claim 1, wherein the spring is a helical spring.

12. The medicament injection device of claim 1, further comprising a medicament cartridge having a penetrable barrier across a distal end thereof and wherein axial movement of the needle holder causes the needle to pierce the penetrable barrier.

13. The medicament injection device of claim 12, wherein the medicament cartridge contains a medicament.

14. The medicament injection device of claim 1, wherein the medicament injection device is an auto-injector device.

15. A method of operating a medicament injection device, the method comprising:
   removing a removable transverse blocking member from the medicament injection device, thereby releasing a spring arranged between a needle holder and a distal end of a needle sleeve of the medicament injection device such that the spring expands to cause the needle holder of the medicament injection device to move proximally into contact with a medicament cartridge and to cause a needle of the medicament injection device to pierce a penetrable barrier of the medicament cartridge.

16. The method of claim 15, further comprising at least partially removing a cap from the medicament injection device in order to release the transverse blocking member prior to removing the transverse blocking member.

17. The method of claim 16, wherein at least partially removing the cap from the medicament injection device comprises at least partially removing a pin of the cap from a recess of the transverse blocking member to release the transverse blocking member.

18. The method of claim 15, wherein removing the transverse blocking member comprises sliding the transverse blocking member out of the medicament injection device.

19. The method of claim 18, wherein sliding the transverse blocking member out of the medicament injection device comprises sliding the transverse blocking member out of an aperture of the needle sleeve of the medicament injection device.

20. The method of claim 19, further comprising initiating an injection of medicament through the needle by axially moving the needle sleeve relative to a main body of the medicament injection device.

* * * * *